United States Patent [19]
Robbins et al.

[11] Patent Number: 5,285,688
[45] Date of Patent: Feb. 15, 1994

[54] SYSTEM FOR DETECTING WOOD-DESTROYING INSECT INFESTATIONS IN WOOD

[75] Inventors: William P. Robbins, St. Paul; Rolf K. Mueller, Stillwater, both of Minn.

[73] Assignee: Regents of the University of Minnesota, Minneapolis, Minn.

[21] Appl. No.: 946,956

[22] Filed: Sep. 17, 1992

[51] Int. Cl.$^5$ .............................................. G01H 1/00
[52] U.S. Cl. .................................................... 73/587
[58] Field of Search ......................... 367/139; 73/587; 43/124, 132.1

[56] References Cited

U.S. PATENT DOCUMENTS

| | | | |
|---|---|---|---|
| 4,809,554 | 3/1989 | Shade et al. | 73/587 |
| 4,895,025 | 1/1990 | Betts | 73/587 |

OTHER PUBLICATIONS

Noguchi et al., "AE Monitoring to detect Termite Attack on Wood of Commercial . . . " Forest Products Journal, vol. 41, #9, Sep. 1991.
The International Research Group on Wood Preservation, "Using AE Monitoring for Detecting Economically Important Species of Termites in California", by Vernard R. Lewis et al., May 20-24, 1991.
In Press USDA Pacific Southwest Forest & Range Exper. Stat. Publication, "The Potential of Using Acoustical Emission to Detect Termites Within Wood", by Vernard R. Lewis et al.
"Characteristics of Acoustic Emission Signals Generated by Termite Activity in Wood", by William P. Robbins et al.
"An Acoustic-Emission-Based Termite Detection System", by William P. Robbins et al.
The International Research Group on Wood Preservation, "Feasibility of AE (Acoustic Emission) Monitoring for the Dectection of the Activities of Wood Destroying Insects", by Yoshihisa Fujii et al., May 10-15, 1992.
"Acoustic Emission Testing to Detect Termites in Structural Timbers", by Thomas John Schaal, pp. 1-58, Mar. 1991.
Product Innovation by Vernard Lewis "Acoustic Emission Device for Termite Detection", p. 26.
"Using Acoustic Emission Monitoring to Detect Termite Activity in Wood", Yoshihisa Fujii et al., (Jan. 1990).
The International Research Group on Wood Preservation, "Detection of Termite Attack in Wood Using Acoustic Emissions", pp. 1-7.
"Anecdotal History of Acoustic Emission From Wood", by Thomas F. Drouillard (Jul. 16, 1990), pp. 1-22.
"The Potential of Using Acoustical Emission to Detect Termites Within Wood", pp. 1-11.

Primary Examiner—Ian J. Lobo
Attorney, Agent, or Firm—Westman, Champlin & Kelly

[57] ABSTRACT

A system for detecting wood-destroying insects by sensing acoustic emissions generated by the insects as they feed. The system comprises two acoustic emission sensors, an amplification section, a signal processing section and an indicator section. The system comes into mechanical contact with the wood to be inspected through the use of a bolt which is inserted into the wood and attaches to an acoustic emission sensor or through the use of an adhesive layer which directly attaches an acoustic emission sensor to the wood. The acoustic emission sensors are electrically connected to the amplification section which is electrically connected to the signal processing section. The signal processing section is capable of distinguishing between insect-caused acoustic emissions and noise-caused acoustic emissions detected by the acoustic emission sensors. The results of the signal processing section are sent to the indicator section.

21 Claims, 7 Drawing Sheets

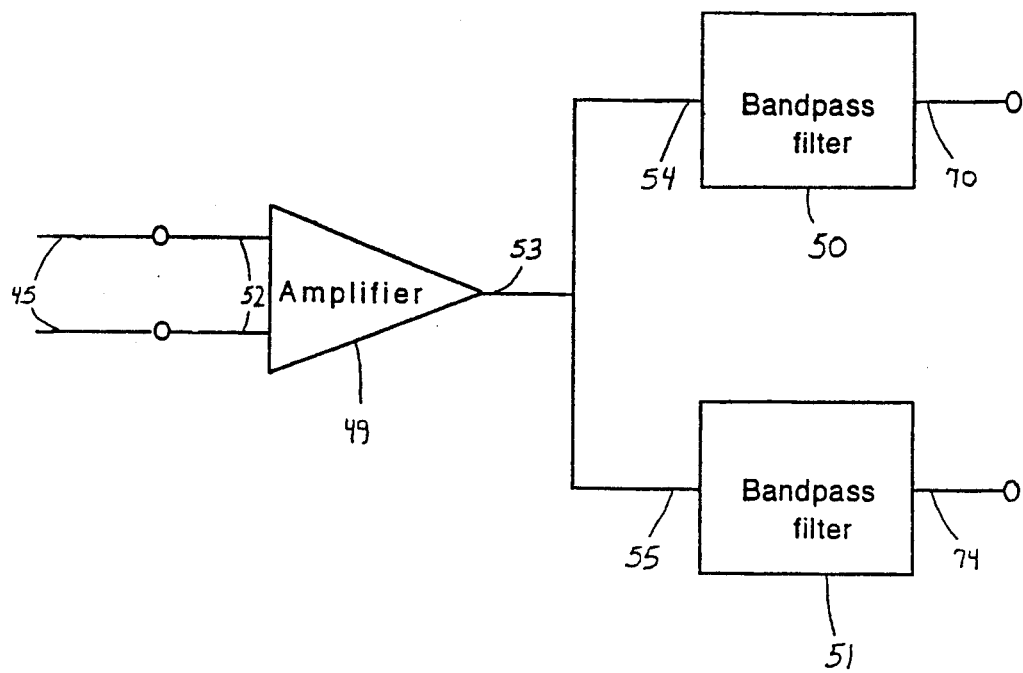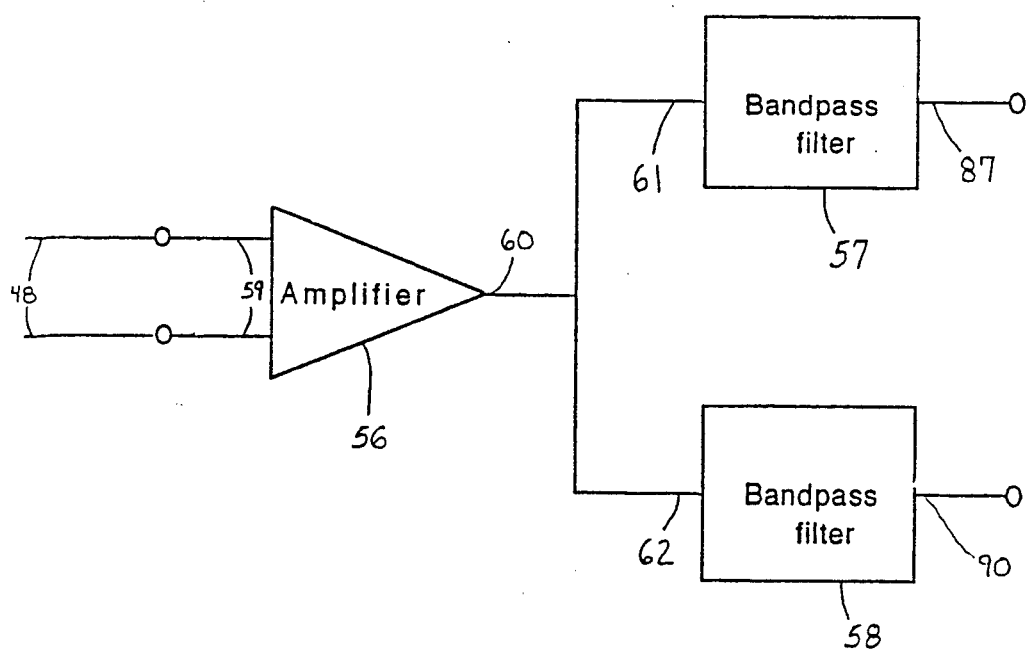
Fig. 5

SYSTEM FOR DETECTING WOOD-DESTROYING INSECT INFESTATIONS IN WOOD

BACKGROUND OF THE INVENTION

The present invention relates to a system for detecting wood-destroying insects in wood and, in particular, to a system that senses the acoustic emissions generated by wood-destroying insects to detect and indicate their presence.

When any of several wood-destroying insects, such as termites, carpenter ants or powder-post beatles, enter a structure constructed partly or wholly of wood, they can cause considerable damage. Preventative measures such as impregnating structural wood with a poison and the application of pesticides to the foundation of a structure have been questioned, and some have even been discontinued, due to environmental concerns. For this reason, the detection and elimination of wood-destroying insects has been a focus of attention in an effort to reduce the damage caused by the insects. The early detection of infestations has become increasingly important as many environmentally safe eradication methods depend upon early detection of an infestation.

The most common method of detecting infestations of wood-destroying insects is visual inspection by a trained professional. Human inspectors must be highly trained and a visual inspection usually reveals an infestation only in its latter stages. In addition, periodic inspections are needed and each inspection is limited to the areas that the inspector can reach or see.

Visual inspection may be supplemented through the use of trained dogs, which detect insects through a combination of smell and sound, sensitive microphones to listen for insect activity, and special purpose gas chromatographs to detect gases given off by insects. However, each of these methods has the drawback of a high cost and an inability to reliably detect a wood-destroying insect infestation.

SUMMARY OF THE INVENTION

The present invention provides a reliable, inexpensive system for detecting wood-destroying insects by sensing the acoustic emissions generated by the insects as they feed. The insect detection system comprises at least one acoustic emission sensor, an amplification section for conditioning electrical signals from the acoustic emission sensor, a signal processing section for determining whether the electrical signals represent insect-caused acoustic emissions, and an indicator section which indicates to the user when the presence of wood-destroying insects has been detected.

The acoustic emission sensor comprises a sealed housing containing a layer of piezoelectric material which can have an acoustically lossy backing. The sensor is mechanically interconnected with the wood to be tested such as through the use of a bolt, an adhesive or other device. The piezoelectric material converts the acoustic energy it receives from the wood into an electrical signal. The amplification section comprises amplifiers to amplify the electrical signal from the acoustic emission sensor and filters to filter out selected frequency components from the electrical signal.

The signal processing section is capable of identifying the source of the acoustic energy received by the acoustic emission sensor as wood-feeding insects by analyzing the magnitude of the electrical signal provided by the acoustic emission sensor in both a high frequency range where most background noises have little energy and a low frequency range where most background noises have high energy. If the magnitude of the signal in the high frequency range is greater than a predetermined value and the magnitude of the signal in the low frequency range is less than a predetermined value, then the signal processing section will identify the source of the acoustic energy received as a wood-destroying insect infestation.

The signal processing section can be placed in more than one mode of operation. A first mode uses two acoustic emission sensors, each placed in contact with the same piece of wood. In this mode, a running total of signals indicating insect-caused acoustic emissions is recorded for each sensor. A second mode also uses two acoustic emission sensors with a first sensor placed in contact with the piece of wood to be tested and a second sensor placed in contact with a reference material known to be free of wood-destroying insects. In this mode, if the signal processing section registers an insect-caused acoustic emission from the second sensor within a predetermined period of time of registering an insect-caused acoustic emission from the first sensor, then the acoustic emission detected by the first sensor will be treated as having been caused by background noise.

The signal processing section sends the results to the indicator section which alerts the user when insect-caused acoustic emissions are detected. The system of the present invention thus provides a method of accurately detecting an infestation of wood-destroying insects at an early stage.

BRIEF DESCRIPTION OF THE DRAWINGS

FIG. 5 is a block diagram of the amplification section of the present invention;

DETAILED DESCRIPTION OF THE PREFERRED EMBODIMENTS

Figure 1:
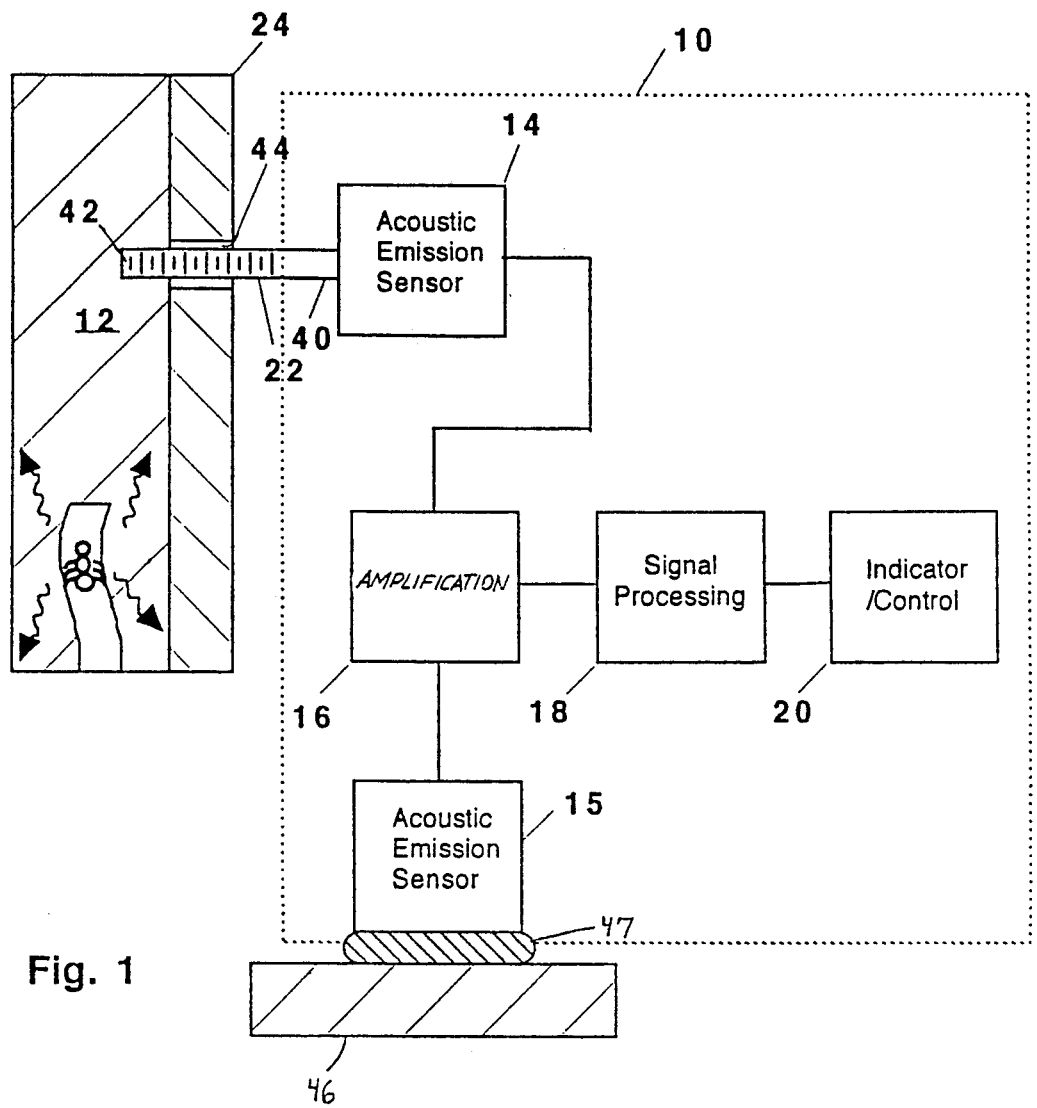
FIG. 1 is a schematic representation of an insect detection system in accordance with the present invention.

A schematic representation of an insect detection system 10 in accordance with the present invention is shown in FIG. 1 in contact with a piece of structural wood 12. The system 10 comprises a first acoustic emission sensor 14, second acoustic emission sensor 15, an amplification section 16, a signal processing section 18 and an indicator/control section 20. The system 10 is interconnected with the wood 12 via a threaded bolt 22 which is attached to the first acoustic emission sensor 14 and can be inserted through an outer wall 24 of the structure being investigated and secured in the wood 12.

Figure 2:
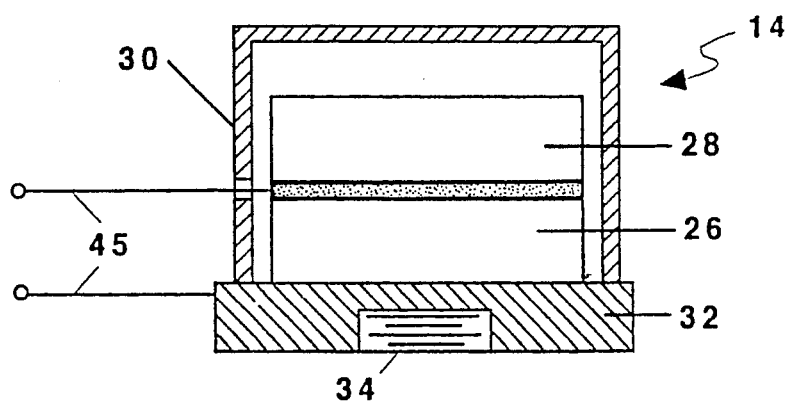
FIG. 2 is a schematic representation of an acoustic emission sensor of the present invention.

The first acoustic emission sensor 14, shown in FIG. 2, comprises a sensing layer 26 made of a piezoelectric material and a backing layer 28 made of an acoustically lossy material hermetically sealed in a sensor housing 30. A first side 32 of the sensor housing 30 has a threaded recess 34 into which a first end 40 of the threaded bolt 22 is screwed. A second end 42 of the threaded bolt 22 is inserted through a hole 44 drilled through any exterior sheathing or coverings, the outer wall 24 shown in FIG. 1, for example, and is screwed into the wood 12. Any acoustic energy in the wood 12 is transmitted through the threaded bolt 22 to the first acoustic emission sensor 14. The sensing layer 26 converts any acoustic energy that impinges on it into an electrical signal, in a known manner. The signal is conducted by two electrical leads 45 which are electrically connected to the sensing layer 26, also in a known manner, and extend from the sensor housing 30.

The second acoustic emission sensor 15 has the same construction as the first acoustic emission sensor 14 except that the first side 32 of the sensor housing 30 is without a recess. The second acoustic emission sensor 15 contacts a piece of wood 46, known to be free of insects, through an adhesive layer 47 placed between the first side 32 of the sensor housing 30 and the wood 46. The adhesive layer 47 can comprise any one of a number of adhesives such as hot melt glue or a pressure sensitive tacky elastomer. Any acoustic energy in the wood 46 is transmitted through the adhesive layer 47 to the second acoustic emission sensor 15. The sensing layer 26 converts any acoustic energy that impinges on it into an electrical signal, in a known manner. The signal is conducted by two electrical leads 48 which are electrically connected to the sensing layer 26, in known manner, and extend from the sensor housing 30.

The sensing layer 26 of each acoustic emission sensor 14,15 is preferably fabricated from lead zirconium titanate, a piezoelectric material, and the backing layer 28 can be fabricated from a variety of acoustically lossy materials. The threaded bolt 22 is normally fabricated from steel, but can also be fabricated from nylon so that the acoustic impedances between the bolt 22 and the wood 12 are substantially matched, improving the transmission of the acoustic emissions between the wood and the bolt 22.

Figure 3:
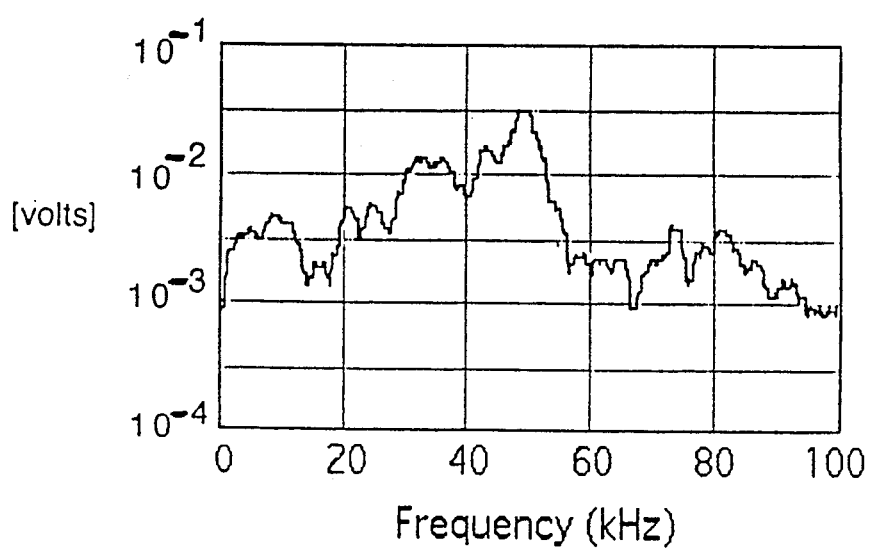
FIG. 3 is a graphic representation of the spectrum of a typical termite caused acoustic emission detected by an acoustic emission sensor in accordance with the present invention.
Figure 4:
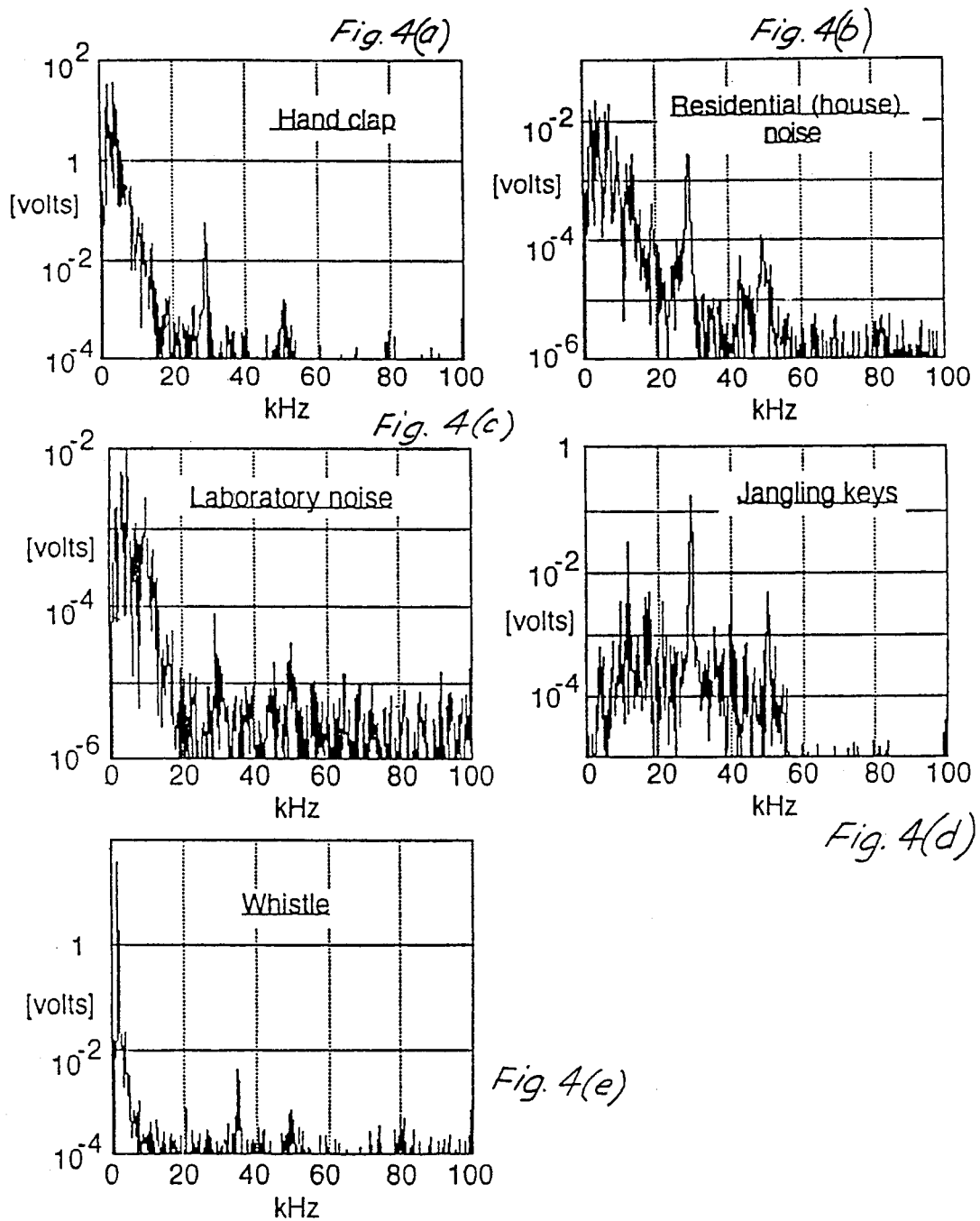
FIGS. 4(a), 4(b), 4(c), 4(d) and 4(e) are graphic representations of the spectra of various noise signals detected by an acoustic emission sensor in accordance with the present invention.

FIG. 3 shows the observed spectral characteristics of an insect-caused electrical signal provided by the acoustic emission sensors 14 and 15 and FIGS. 4(a), 4(b), 4(c), 4(d) and 4(e) show the spectral characteristics of several noise-related signals provided by the acoustic emission sensors 14 and 15. An examination of FIGS. 3 and 4(a), 4(b), 4(c), 4(d) and 4(e) shows that the insect-caused signals have a smaller magnitude in the frequency range below 45 kHz than do the signals caused by the observed noises. However, the insect-caused signals have a greater magnitude than the noise signals in the frequency range between 45 kHz and 65 kHz (called insect present frequency). These observations were used to develop the amplification section 16 and the signal processing section 18 of the insect detection system 10.

A first portion of the amplification section 16, shown in FIG. 5, comprises a first amplifier 49, a first filter 50 and a second filter 51. The electrical leads 45 from the first acoustic emission sensor 14 are electrically connected to an input 52 of the first amplifier 49 such that the electrical signals provided by the first acoustic emission sensor 14 are conducted to the first amplifier 49. An output 53 of the first amplifier 49 is electrically connected to both an input 54 of the first filter 50 and an input 55 of the second filter 51.

A second portion of the amplification section 16 comprises a second amplifier 56, a third filter 57 and a fourth filter 58. The electrical leads 48 from the second acoustic emission sensor 15 are electrically connected to an input 59 of the second amplifier 56 such that the electrical signals provided by the second acoustic emission sensor 15 are conducted to the second amplifier 56. An output 60 of the second amplifier 56 is electrically connected to both an input 61 of the third filter 57 and an input 62 of the fourth filter 58.

The electrical signals from the first and second acoustic emission sensors 14,15 which are caused by insect activity typically have a wide bandwidth and an amplitude typically between 10 and 100 microvolts. Therefore, the first amplifier 49 and the second amplifier 56 must be low noise amplifiers having a bandwidth of approximately 100 kHz or greater and a gain of approximately 60 decibels. The first and third filters 50,57 are typically 55 kHz bandpass filters having a bandwidth of 10 kHz. Most background noises in the frequency range passed by the first and third filters 50,57 have little energy. The second and fourth filters 51,58 are typically 10 kHz bandpass filters having a bandwidth of 1 kHz. Most background noises in the frequency range passed by the second and fourth filters 51,58 have high energy. The exact magnitudes of the filter passbands are not critical and those specified here were chosen for convenience. The amplification section 16 thus isolates a low frequency and a high frequency component of the electrical signals provided by the first and second acoustic emission sensors 14,15.

The first and third filters 50,57 filter out the frequency components of the electrical signals below 45 kHz which are caused increasingly by non-insect sources of acoustic emissions and above 65 kHz which are primarily caused by electronic noise in the system. The second and fourth filters 51,58 pass a section of the frequency spectrum caused primarily by non-insect noise (called "non-insect frequency").

Figure 6:
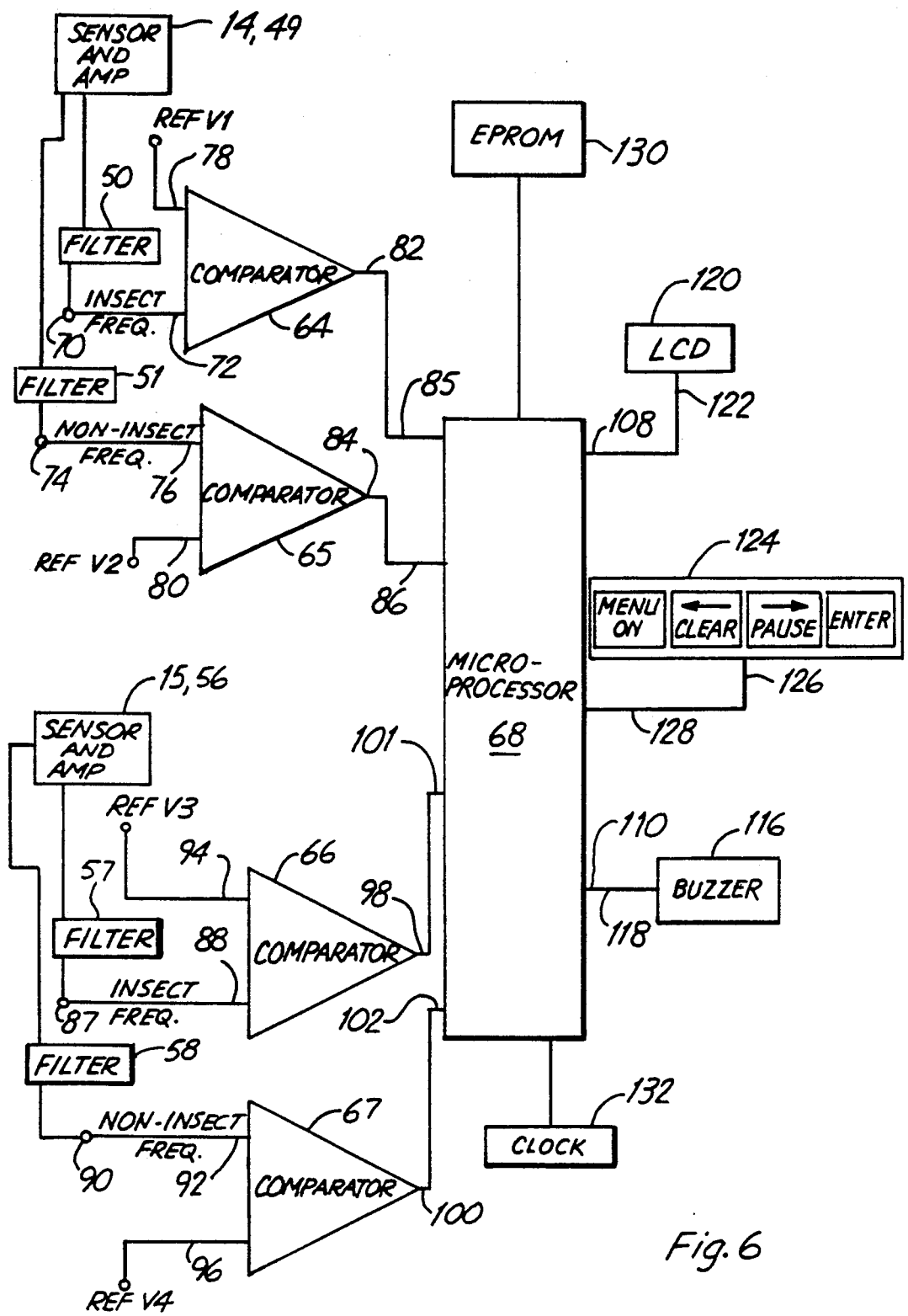
FIG. 6 is a block diagram of the signal processing section and the indicator/control section of the present invention.

The signal processing section 18, shown in FIG. 6, comprises a first comparator 64, a second comparator 65, a third comparator 66, a fourth comparator 67 and a microprocessor 68. An output 70 of the first filter 50 is electrically connected to a first input 72 of the first comparator 64 while an output 74 of the second filter 51 is electrically connected to a first input 76 of the second comparator 65. A first predetermined reference voltage is electrically connected to a second input 78 of the first comparator 64 and a second predetermined reference voltage is electrically connected to a second input 80 of the second comparator 65.

Figure 8:
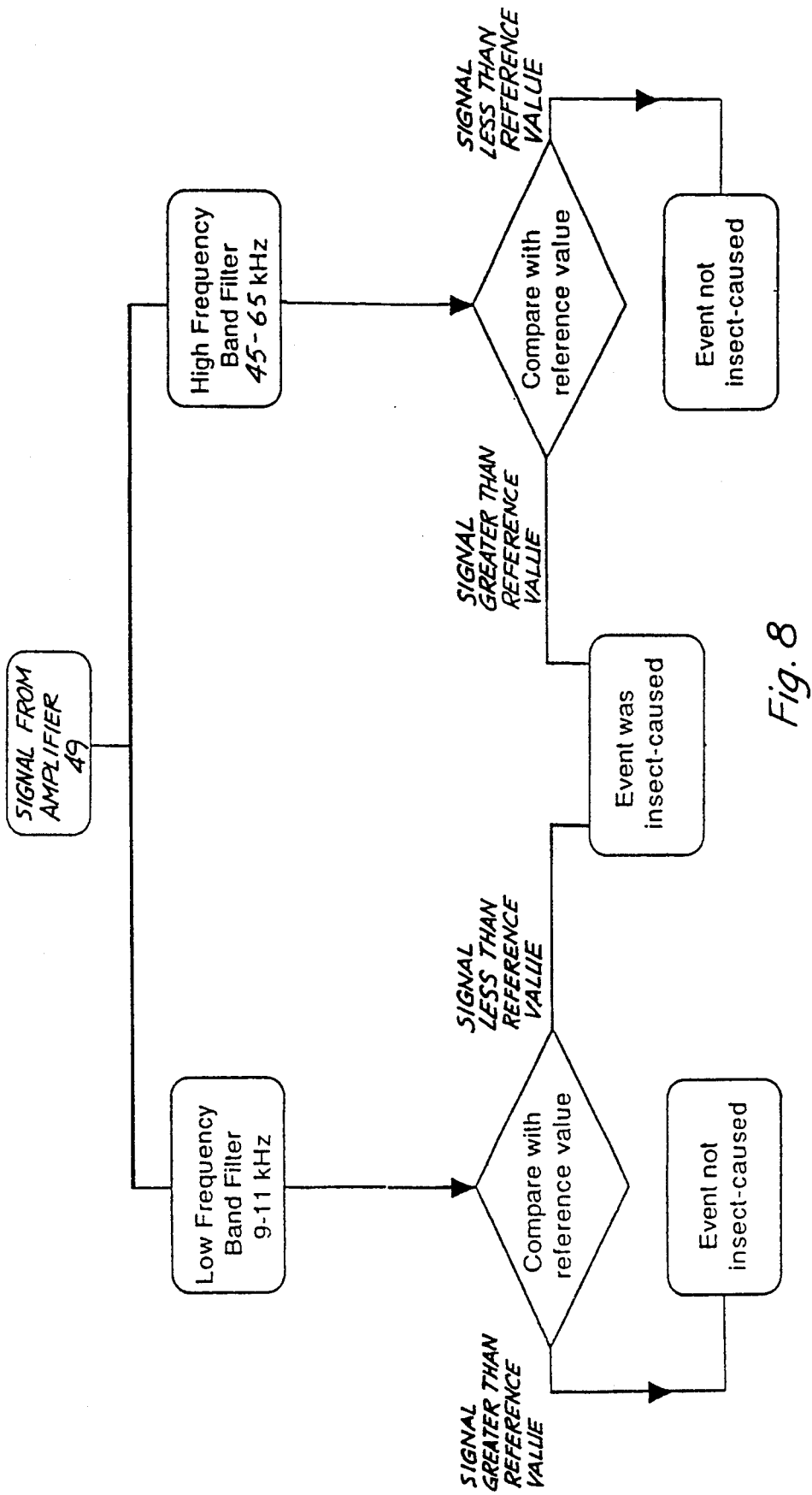
FIG. 8 is a block diagram of a portion of the signal processing section of the present invention.

The magnitude of the first reference voltage is an adjustable threshold value which is set at a level (magnitude) above which any signal provided by the first bandpass filter 50 is considered to be caused by a signal source other than electronic noise, and below which any signal provided by the first bandpass filter 50 is considered to be caused by noise. The magnitude of the second reference voltage is an adjustable threshold value which is set at a level (magnitude) above which any signal provided by the second bandpass filter 51 is considered to be caused by non-insect noise and below which any signal provided by the second bandpass filter 51 is considered to be caused by indeterminable sources. This is illustrated by the algorithm shown in FIG. 8.

Whenever the magnitude of the electrical signal input to a comparator from a bandpass filter output exceeds the threshold (reference) voltage input to that comparator, the comparator output changes from a low voltage (logic zero) to a high voltage (logic one) and remains at the high voltage until the input signal magnitude from the bandpass filter falls below the threshold voltage value.

If the magnitude of the signal at the first input 72 of the first comparator 64 is greater than the magnitude of the signal at the second input 78, the first comparator 64 will provide a high (logic one) signal at an output 82. If the magnitude of the signal at the first input 76 of the second comparator 65 is greater than the magnitude of the signal at the second input 80, the second comparator 65 will provide a high (logic one) signal at an output 84 (indicating a signal caused by non-insect noise). The first and second comparators 64,65 will each continue to provide a high signal until the magnitude of the signal at the respective first input 72,76 falls below the reference voltage at the respective second input 78,80. The outputs 82,84 of the first and second comparators 64,65 are electrically connected to first and second inputs 85,86 of the microprocessor 68, respectively.

An output 87 of the third filter 57 is electrically connected to a first input 88 of the third comparator 66 while an output 90 of the fourth filter 58 is electrically connected to a first input 92 of the fourth comparator 67. A third predetermined reference voltage is electrically connected to a second input 94 of the third comparator 66 and a fourth predetermined reference voltage is electrically connected to a second input 96 of the fourth comparator 67. The magnitudes of the third and fourth reference voltages are adjustable threshold values which are generally set at levels equal to the first and second reference voltages respectively.

When the magnitude of the signal at the first input 88 of the third comparator 66 is greater than the magnitude of the signal at the second input 94, the third comparator 66 will provide a high (logic one) signal at an output 98. If the magnitude of the signal at the first input 92 of the fourth comparator 67 is greater than the magnitude of the signal at the second input 96, the fourth comparator 67 will provide a high (logic one) signal at an output 100 (indicating a signal caused by non-insect noise). The third and fourth comparators 66,67 will each continue to provide a high signal until the magnitude of the signal at the respective first input 88,92 falls below the reference voltage at the respective second input 94,96. The outputs 98,100 of the third and fourth comparators 66,67 are electrically connected to third and fourth inputs 101,102 of the microprocessor 68, respectively.

The comparator outputs 82, 84, 98 and 100, which are inputs 85, 86, 101 and 102 to the microprocessor 68 are evaluated by the microprocessor under the instructions from a stored program in an EPROM 130 which is electrically connected to the microprocessor 68. The results of this evaluation are used to update the indications that insects are present. The stored program in the EPROM 130 provides a frequency separation noise rejection scheme and permits operation in two separate modes which are described later. The manner in which the evaluation of the microprocessor inputs from the comparators is accomplished is described below.

The microprocessor 68 is programmed so that upon receiving a high signal at its first input 85 or its third input 101 (insect present frequency), the microprocessor 68 will ignore any subsequent changes in that signal from high to low for a predetermined period of time. The period of time is set long enough so that the normal fluctuations of a typical acoustic emission are not recorded as separate emissions and is set short enough so that subsequent valid insect-caused emissions will not be missed.

If the signal at the first input 85 is high (insect present frequency), and the signal at the second input 86 remains low (logic zero meaning no high non-insect noise) for 50 milliseconds centered about the time when the signal at the first input 85 became high (+25 milliseconds), the microprocessor 68 will register the detection of an insect-caused acoustic emission by the first acoustic emission sensor 14. If the signal at the third input 101 is high (sensor 15 also detects insect present frequency), and the signal at the fourth output 102 remains low (no high background non-insect noise) for 50 milliseconds centered about the time the third input 101 became high, the microprocessor 68 will register the detection of an insect-caused acoustic emission by the second acoustic emission sensor 15.

In a first mode of operation called a total count mode, both sensors 14 and 15 are placed on the same piece of wood 12 and a running total of valid signals indicating an insect-caused acoustic emission is recorded for each sensor. The acoustic emission sensor that records the larger number of counts in a given time period is very likely the nearest to the insect infestation. In this mode, both sensors 14 and 15 may record some noise events such as jangling keys, finger snaps, hand claps, and other explosive or impulsive-like noises in spite of the operation of the frequency separation noise rejection comparators.

In most cases, the operator should be able to distinguish whether or not the events recorded on a display 120 are caused by insects or other noise events. If the display 120 seems to increment (count) most of the time only when an audible sound is heard, then the active sensor is probably not picking up insect-caused acoustic emissions. If this is the case, then the operator should switch to a second operating mode, the spatial separation noise rejection mode.

In this case, sensor 15, which is placed on an insect free piece of wood 46, is used as a reference sensor. If the microprocessor 68 registers the detection of an insect-caused acoustic emission by the second or reference acoustic emission sensor 15 within a predetermined length of time of the detection of an insect-caused acoustic emission by the first or active acoustic emission sensor 14, the emission detected by the first acoustic emission sensor 14 will be treated as a noise event not caused by insects, because both the active and reference sensors detect the same frequency noise. Any detection of a noise in the "insect present" frequency by the second acoustic emission sensor 15, which is on the insect-free wood 46, is therefore most likely some background noise which also affected the first acoustic emission sensor 14. If the signal generated by the second acoustic emission sensor 15 does not indicate an insect-caused acoustic emission, the microprocessor 68 will provide a signal at a first output 108 and a second output 110 indicating a valid detection of an insect-caused acoustic emission by the first acoustic emission sensor 14.

This mode of operation is essentially a differential operating mode or, in life sciences jargon, an experiment with a control (the uninfested wood sample being compared to the suspected sample). Proper operation of this mode can be verified by deliberately creating some background noise (jangling keys, snapping fingers, etc.) and noting that few, if any, of them register on the display 120 compared to the larger number that do when the unit is in the second or total count mode.

A keyboard 124 is used to turn the system 10 on and off and to select the mode of operation of the microprocessor 68 from an operating menu displayed on the liquid crystal display 120. Upon activating the insect detection system 10, the display 120 will display an initial message for a brief period of time followed by the operating menu. After the mode of operation is selected using the keyboard 124, the display 120 will show the total number of insect-caused acoustic emissions. The mode can be changed at any time by pressing the menu ON key on the keyboard 124 to display the operating menu.

The indicator/control section 20, shown in FIG. 6, comprises a buzzer 116 having an input 118 electrically connected to the secnd output 110 of the microprocessor 68, the liquid crystal display 120 having an input 122 electrically connected to the first output 108 of the microprocessor 68 and the keyboard 124 having an output 126 electrically connected to a fifth input 128 of the microprocessor 68. Upon the provision of a signal from the second output 110 of the microprocessor 68, the buzzer 116 is activated for a short period of time, indicating the detection of an insect-caused acoustic emission. The liquid crystal display 120 shows a running total of the number of insect-caused acoustic emissions detected by either the first and second acoustic emission sensors 14,15 in the first mode or the first acoustic emission sensor 14 in the second mode. It is incremented upon the provision of a signal from the first output 108 of the microprocessor 68. The number of audible sounds from the buzzer 116 and the total number of insect-caused acoustic emissions shown on the liquid crystal display 120 provide the user with the information required to determine the size of an infestation.

In any of the operating modes, the liquid crystal display 120 can be reset to zero by pressing the CLEAR key on the keyboard 124. In addition, the operation of the microprocessor 68 can be interrupted and then resumed by pressing the PAUSE key on the keyboard 124. The use of the EPROM 130 allows the manner in which the signal processing section 18 operates to be changed without changing its physical structure. A clock generator 132 is electrically connected to the microprocessor 68 and provides a clock signal for the signal processing section 18.

Figure 7:
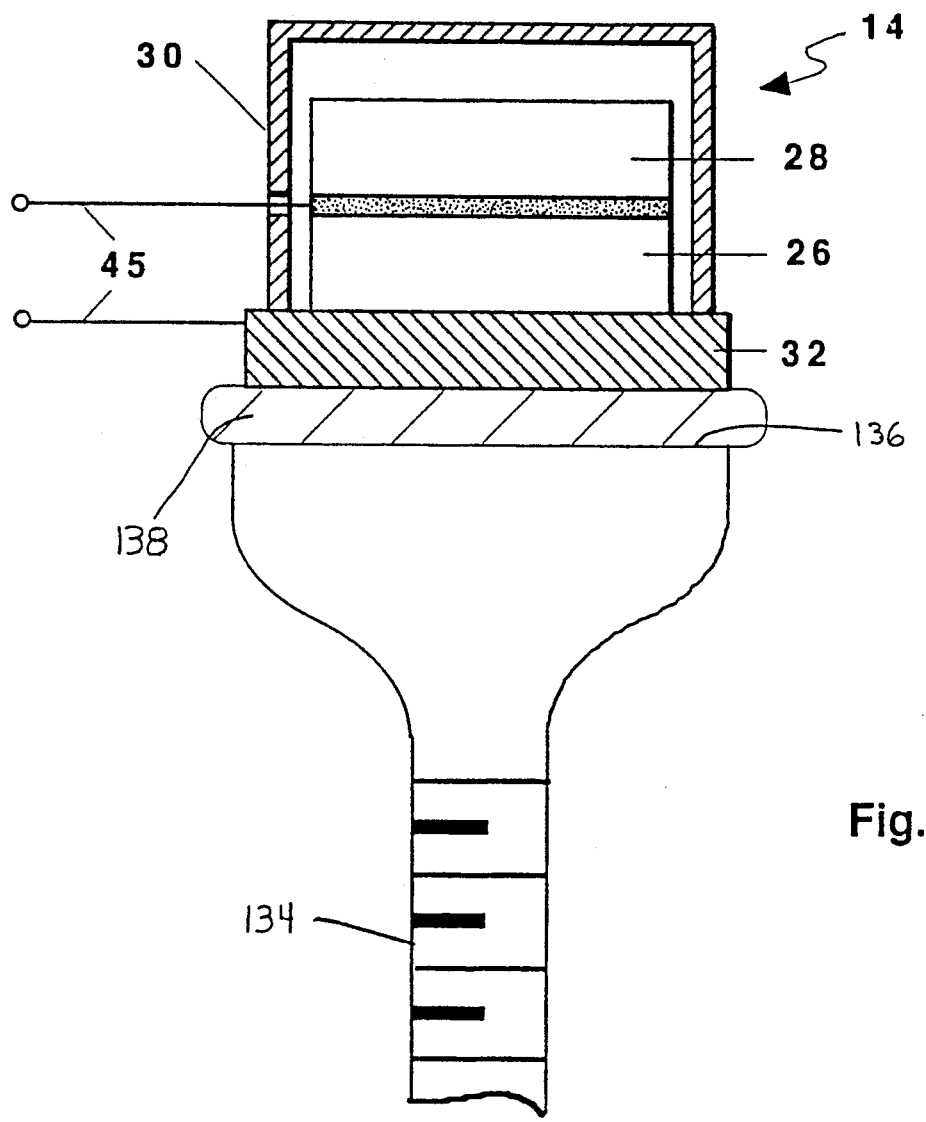
FIG. 7 is a schematic representation of an acoustic emission sensor of the present invention mounted on a bolt with a taper for improved sound transmission to the sensor.

Although the first acoustic emission sensor 14 was described as being attached to the wood 12 through the use of the threaded bolt 22, the first acoustic emission sensor 14 an be attached to the wood 12 through a bolt 134, shown in FIG. 7, having a flat end 136 attached to the first side 32 of the sensor housing 30 by an adhesive layer 138. The bolt 134 is inserted into the wood 12 in the same manner as the bolt 22. he bolt 134 has a tapered cross-section to improve acoustic signal transmission to the first acoustic emission sensor 14. In addition to the use of a bolt, the first acoustic emission sensor 14 can contact the wood 12 through the use of an adhesive layer. an adhesive layer is used instead of the bolts 22,134 when the wood 12 is directly accessible and not covered by an exterior sheathing such as the outer wall 24.

Although the present invention has been described with reference to preferred embodiments, workers skilled in the art will recognize that changes may be made in form and detail without departing from the spirit and scope of the invention.

What is claimed is:

1. A system for detecting infestations of wood-destroying insects in wood, the system comprising:
   an acoustic emission sensor having an output, the acoustic emission sensor being responsive to acoustic emissions in wood and comprising means for converting the acoustic energy of the acoustic emissions into an electrical signal and providing the electrical signal at its output;
   contact means for placing the acoustic emission sensor into mechanical contact with a piece of wood to be tested;
   signal processing means having an input and having an output, the signal processing means including means for analyzing the spectral characteristics of the electrical signal provided by the acoustic emission sensor to determine whether the electrical signal provided by the acoustic emission sensor is caused by acoustic emissions from a wood-destroying insect infestation; and
   indicating means having an input which is electrically connected to the signal processing means output for indicating to a user when the signal processing means has determined that the electrical signal provided by the acoustic emission sensor is caused by acoustic emissions from a wood-destroying insect infestation.

2. The apparatus of claim 1 wherein the signal processing means input is electrically connected to the acoustic emission sensor output.

3. The apparatus of claim 1 and amplification means having an input which is electrically connected to the acoustic emission sensor output and having an output, the amplification means increasing the amplitude of the electrical signal provided by the acoustic emission sensor.

4. The apparatus of claim 3 wherein the signal processing means input is electrically connected to the amplification means output.

5. The apparatus of claim 3 and filtering means having an input which is electrically connected to the amplification means output and an output which is electrically connected to the signal processing means input, for extracting a low frequency component, in which most background noises have high energy, and a high frequency component, in which most background noises have little energy, from the electrical signal provided by the acoustic emission sensor.

6. The apparatus of claim 5 wherein the filtering means comprises a first bandpass filter for passing to its output a high frequency component of the electrical signal provided by the acoustic emission sensor in which most background noises have little energy and a second bandpass filter for passing to its output a low frequency component of the electrical signal provided by the acoustic emission sensor in which most background noises have high energy.

7. The apparatus of claim 6 wherein the signal processing means determines that the electrical signal provided by the acoustic emission sensor is caused by acoustic emissions other than from a wood-destroying insect infestation when the magnitude of the frequency components passed by the second filter exceeds a threshold value having a magnitude above which frequency components passed by the second filter are caused by non-insect noise.

8. The apparatus of claim 1 and a second acoustic emission sensor having an output, the second acoustic emission sensor being responsive to acoustic emissions in wood and comprising means for converting the acoustic energy of the acoustic emissions into an electrical signal and providing the electrical signal at its output.

9. The apparatus of claim 8 and second contact means for placing the second acoustic emission sensor into mechanical contact with wood.

10. The apparatus of claim 9 wherein the signal processing means has a second input and includes second means for analyzing the spectral characteristics of the electrical signal provided by the second acoustic emission sensor to determine whether the electrical signal provided by the second acoustic emission sensor is caused by acoustic emissions from a wood-destroying insect infestation.

11. The apparatus of claim 10 wherein the second signal processing means input is electrically connected to the output of the second acoustic emission sensor.

12. The apparatus of claim 10 and second amplification means having an input which is electrically connected to the second acoustic emission sensor output and having an output, the second amplification means increasing the amplitude of the electrical signal provided by the second acoustic emission sensor.

13. The apparatus of claim 12 and second filtering means having an input which is electrically connected to the second amplification means output and an output which is electrically connected to the second signal processing means input, for extracting a low frequency component, in which most background noises have high energy, and a high frequency component, in which most background noises have little energy, from the electrical signal provided by the second acoustic emission sensor.

14. The apparatus of claim 13 wherein the second filtering means comprises a first bandpass filter for passing to its output a high frequency component of the electrical signal provided by the second acoustic emission sensor in which most background noises have little energy and a second bandpass filter for passing to its output a low frequency component of the electrical signal provided by the second acoustic emission sensor in which most background noises have high energy.

15. The apparatus of claim 14 wherein the signal processing means determines that the electrical signal provided by the second acoustic emission sensor is caused by acoustic emissions other than from a wood-destroying insect infestation when the magnitude of the frequency components passed by the second filter exceeds a threshold value having a magnitude above which frequency components passed by the second filter are caused by non-insect noise.

16. The apparatus of claim 10 wherein the second acoustic emission sensor is placed into mechanical contact with the piece of wood to be tested.

17. The apparatus of claim 10 wherein the second acoustic emission sensor is placed into mechanical contact with a reference material known to be free of wood-destroying insects.

18. The apparatus of claim 17 wherein the signal processing means prevents the indicating means from indicating to a user that the electrical signal provided by the first mentioned acoustic emission sensor is caused by acoustic emissions from a wood-destroying insect infestation when the electrical signal provided by the second acoustic emission sensor indicates that it is caused by acoustic emissions from a wood-destroying insect infestation.

19. The apparatus of claim 1 wherein the acoustic emission sensor comprises a layer of a piezoelectric material and a layer of an acoustically lossy material contained within a housing.

20. The apparatus of claim 1 and further comprising a visual display having an input which is electrically connected to the signal processing means output, the visual display being capable of displaying the number of acoustic emissions that are caused by wood-destroying insects.

21. The apparatus of claim 1 and an audible indicator having an input which is electrically connected to the signal processing means output, the audible indicator being capable of generating a tone of short duration each time an insect-caused acoustic emission is detected by the acoustic emission sensor.

* * * * *